United States Patent [19]

Burton et al.

[11] 4,062,801

[45] Dec. 13, 1977

[54] CATALYST REGENERATION METHOD

[75] Inventors: Vance P. Burton, Arlington Heights; Michael Z. Mikulicz, Palatine, both of Ill.

[73] Assignee: VOP Inc., Des Plaines, Ill.

[21] Appl. No.: 751,421

[22] Filed: Dec. 16, 1976

Related U.S. Application Data

[63] Continuation-in-part of Ser. No. 605,561, Aug. 11, 1975, abandoned, which is a continuation-in-part of Ser. No. 475,686, June 3, 1974, abandoned.

[51] Int. Cl.$^2$ .................. B01J 27/28; B01J 21/20; C07C 3/10
[52] U.S. Cl. .................. 252/414; 260/683.15 C
[58] Field of Search .................. 252/414; 208/216; 260/683.15 C

[56] References Cited

U.S. PATENT DOCUMENTS

| | | | |
|---|---|---|---|
| 1,955,253 | 4/1934 | Russell et al. | 252/414 |
| 2,234,177 | 3/1941 | Kanhofer | 252/414 |
| 2,658,059 | 11/1953 | Peters et al. | 252/414 |
| 2,658,933 | 11/1953 | May et al. | 252/414 |
| 3,375,293 | 3/1968 | Breckoff et al. | 252/414 |
| 3,505,206 | 4/1970 | Decker | 252/414 |
| 3,505,207 | 4/1970 | Haney et al. | 252/414 |
| 3,772,211 | 11/1973 | Mounce | 252/414 |
| 3,823,085 | 7/1974 | Kochie | 208/216 |

*Primary Examiner*—Patrick P. Garvin
*Assistant Examiner*—P. E. Konopka
*Attorney, Agent, or Firm*—James R. Hoatson, Jr.; John F. Spears, Jr.; William H. Page, II

[57] ABSTRACT

Solid catalysts including solid phosphoric acid catalysts are regenerated in-situ in a multi-step method. A sequence which includes depressurization, soaking in an aromatic hydrocarbon-containing liquid at a high temperature and pressure, depressurization and draining is repeated three times. The regeneration removes polymers formed from olefinic reactants.

4 Claims, No Drawings

CATALYST REGENERATION METHOD

CROSS-REFERENCE TO RELATED APPLICATIONS

This application is a continuation-in-part of our prior application Ser. No. 605,561 filed on Aug. 11, 1975, now abandoned, which was a continuation-in-part of our prior application Ser. No. 475,686 filed June 3, 1974 and now abandoned.

FIELD OF THE INVENTION

The invention relates to a method of regenerating a solid catalyst. More specifically the invention relates to a method of regenerating a solid catalyst by removing polymers and to a method of regenerating a solid phosphoric acid catalyst which has been contacted with an olefin-containing reactant stream.

PRIOR ART

In a sizable number of petroleum and petrochemical processes an olefin-containing reactant stream is passed through a fixed bed of a solid catalyst for the purpose of reacting the olefins with themselves or with another hydrocarbon contained in the reactant stream. One example of this is polymerization of $C_3$ and $C_4$ olefins to form motor fuel or to produce $C_7$, $C_9$ and $C_{12}$ olefins. This process is also referred to as oligomerization or catalytic condensation. The product olefins are used in the production of a number of intermediate chemicals and end products including alcohols, detergents and plastics. Another example is the reaction of olefins with aromatic hydrocarbons, normally benzene, to form cumene, ethylbenzene and cymene. Cumene is used in the manufacture of phenol and acetone, and ethylbenzene is consumed in the production of styrene. Cymene (isopropyl toluene) is used directly in the manufacture of solvents and resins and as an intermediate in the production of cresol. These processes are practiced commercially, and those skilled in the art are therefore familiar with their design and operation.

It has been recognized in the art that when solid catalysts are used for effecting the reaction of olefins an undesirable layer of polymers gradually forms on the surface of the catalyst. This eventually lowers the activity of the catalyst or clogs the reactant passageways through the catalyst bed to the point that the process cannot be operated economically. One problem caused by polymerization is unique to slurry type reactors. This type of reactor is filled with an agitated slurry or suspension of finely divided catalyst particles in a dense hydrocarbon liquid phase. The catalyst particles tend to agglomerate and sink to the bottom of the reactor after extended periods of operation. In U.S. Pat. No. 2,658,933 this problem is solved by selectively removing the agglomerated catalyst from the reaction zone, washing the agglomerated catalyst with a suitable solvent, and then returning the catalyst to the reactor. The preferred solvents are relatively low boiling aromatic hydrocarbons having a single aromatic ring. The reference is directed to the production of gasoline boiling range polymers. In describing the prior art the reference refers to another application, which is presumably also directed toward a slurry reactor system, in which agglomeration is taught to be prevented by washing the catalyst continuously or intermittently with an aromatic solvent.

In U.S. Pat. No. 2,658,059 a process for polymerizing ethylene to produce gasoline is presented. This process uses fixed beds of catalyst which are alternately operated in a swing reactor system. Polymers which form on the catalyst are removed in an "extraction" step in which the catalyst is washed with a solvent such as monocyclic aromatic hydrocarbons. The solvent is continuously passed downward through the catalyst bed at a temperature usually between about 85° C. and about 150° C. under a pressure to maintain the solvent in a liquid phase. The preferred catalyst in this process comprises nickel and cobalt supported on an activated charcoal carrier.

In U.S. Pat. No. 3,505,206 the problem of catalyst bed fouling during the hydrotreating heavy or residual mineral oils is addressed. The solution presented in this reference is the upward in-situ washing of the catalyst with a liquid having a boiling point below about 800° F. and the ability to dissolve asphaltenes. Aromatic hydrocarbons such as benzene are described as suitable solvents. The upward flow is to be at a velocity sufficient to cause the expansion of the catalyst by at least 1 vol.% and preferably at least 5-10 vol.%. This expansion is to loosen fines which are carried from the reactor in the upward flowing solvent. The entire catalyst bed may be agitated in such a manner that a top to bottom circulation of the catalyst particles is achieved.

U.S. Pat. No. 3,505,207 describes a method of dealing with the fouling of catalyst beds used in the hydroconversion of shale oils. An initial catalyst bed is intermittently washed with an aromatic hydrocarbon solvent which is passed upward through the bed at a rate sufficient to cause an expansion in the volume of the bed of at least 1 vol.%. It is preferred that washing occur without depressurizing the reactor below about 500 psig. to avoid a temporary decrease in catalyst activity. Preferably, hydrogen or an inert gas is used to supplement the solvent flow. It is taught that the solvent flow may be terminated while the catalyst bed is agitated by a gas stream and the dirty solvent drained off and replaced. This cycle is repeated until the catalyst is clean.

In U.S. Pat. No. 3,823,085 a method of maintaining the activity of a catalyst used to hydrotreat a liquid petroleum feed is described. This method comprises reducing the reactor pressure at the rate of approximately one-eighth of the total pressure per hour for about one-half hour to about six hours while the feed stream is still passed through the reactor. The minimum reduced pressure specified in this reference is 100 psig. or the vapor point of the feed.

BRIEF SUMMARY OF THE INVENTION

The invention provides an in-situ regeneration method for solid catalyst on which polymers have been deposited during the processing of an olefin-containing feed stream. A broad embodiment of the invention comprises the steps of depressurizing the catalyst from a pressure above about 300 psig. to below about 10 psig.; immersing the catalyst bed in a hot aromatic hydrocarbon-containing liquid by passing the liquid upward into the catalyst bed; pressurizing the catalyst bed and soaking the catalyst bed for at least 30 minutes at a temperature above about 280° F.; and depressurizing and draining the catalyst. These steps are performed three times. The subject method has been found to be effective in the regeneration of SPA catalysts.

DETAILED DESCRIPTION

The present invention has broad application in the petroleum and petrochemical industries. It may generally be applied to solid catalysts which have been used to effect the reaction of olefinic hydrocarbons. These previously described reactions include the polymerization or oligomerization of olefins to produce motor fuel, propylene-trimer, propylene-tetramer and heptanes. This is described in U.S. Pat. Nos. 2,234,177 and 2,658,933. Olefins are also reacted with aromatic hydrocarbons. For instance, benzene may be alkylated to produce ethylbenzene and with propylene to produce cumene. The latter process is often used in conjunction with an oxidation operation to produce phenol as described in the article appearing at page 91 of the March, 1976 edition of *Hydrocarbon Processing*.

A catalyst which is often used in these processes is commonly referred to as an SPA (solid phosphoric acid) catalyst. The regeneration of this type of catalyst is the preferred embodiment of the invention. The term "SPA catalyst" or its equivalent is intended to refer generically to a catalyst which contains as one of its principal raw ingredients an acid of phosphorus such as ortho-, pyro- or tetraphosphoric acid. An SPA catalyst is normaly formed by mixing the acid of phosphorus with a siliceous solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide have been added to the carrier to increase its strength and hardness. The combination of the carrier and the additives normally comprises about 15–30% of the catalyst, with the remainder being the phosphoric acid. However, the amount of phosphoric acid used in the manufacture of the catalyst may vary from about 8–80 wt.% of the catalyst as described in U.S. Pat. No. 3,402,130. The additive may comprise about 3–20% of the total carrier material. SPA catalysts are available commercially. Further details as to the composition and production of SPA catalysts may be obtained from U.S. Pat. Nos. 3,050,472; 3,050,473 and 3,132,109 and from other references.

SPA catalysts differ from those catalysts which are formed by the placement of catalytic substances on a refractory support. This latter type of catalyst may be exemplified by those solid catalysts used in fixed bed hydrodesulfurization and hydrocracking operations. When they become unsuitably covered with carbonaceous deposits, they are normally subjected to a high temperature oxidation operation in which these deposits are actually burned off the catalyst. It is not desirable to perform such an oxidation procedure on an SPA catalyst. The typical SPA catalyst is much less structurally stable than the refractory based catalysts. For instance, the loss of moisture causes deterioration of the catalyst by powdering and caking, ultimately causing a high pressure drop through the bed and the termination of processing. On the other hand, when excessive moisture enters the reaction the catalyst softens and tends to form a sludge. This difference in physical stability and chemical structure prevents the usage of many refractory catalyst regeneration procedures on SPA catalysts. In particular, the high temperature combustion methods have not been successful when applied to SPA catalysts due to the dehydration of the catalysts.

Other catalyst systems for the reaction of olefins are known. It is believed the subject invention may also find utility in their regeneration. For instance, in previously cited U.S. Pat. No. 2,658,059 the preferred polymerization catalyst comprises cobalt, nickel or cobalt-nickel mixtures supported on an activated carbon carrier material. Still different catalyst systems are described in U.S. Pat. Nos. 3,981,940 and 3,981,941.

Processes in which an olefin-containing reactant stream is passed over a bed of reaction-promoting solid catalyst are often troubled by the deposition of polymers. This is true of SPA catalysts used in the previously described polymerization and alkylation processes. Polymer deposition has two undesirable results. First, it increases the pressure drop through the catalyst bed. This by itself can force the premature shut-down of the process. The reasons for a premature shut-down include that a high pressure drop may cause damage to the internal structure of the reactor containing the catalyst bed and that it definitely increases the utility costs of operating the process. Eventually, the pressure drop will exceed the capability of the compressors to maintain the desired flow rates. Shut-downs caused by a high pressure drop across the catalyst bed may be described as premature since the overall activity of the catayst in the reactor is still sufficient to operate the process. However, the second undesirable result of polymer deposition is a decrease in catalyst activity. It is an objective of this invention to provide an in-situ method of regenerating a fixed bed of solid catalyst which has been used to react an olefin-containing feed stream. It is a further objective of this invention to provide a method for the in-situ regeneration of a fixed bed of SPA catalyst.

The processes in which the subject invention may be employed normally operate at an elevated pressure above about 300 psig. Higher pressures of 500 to 1000 psig. are also used, as in the production of cumene. The catalyst bed will be maintained at an elevated temperature above 250° F. and normally from about 400° to 500° F. The first step in the subject regeneration method is to terminate the flow of the reactant feed stream through the catalyst bed and to drain any residual liquids from the catalyst step. This step is preferably performed with as small a decrease in the temperature and pressure of the catalyst bed as is practical. The catalyst bed should be at a pressure above about 300 psig. and at a temperature above about 280° F. at the completion of this step. In the preferred embodiment, the catalyst bed is maintained at a temperature above about 325° F. and a pressure above about 400 psig. while it is isolated and drained. The catalyst can be swept with a hot gas, such as propane, if desired to promote drainage of any liquid present in the reactor.

The next step in the subject method is to depressurize the catalyst bed, preferably to a pressure below about 10 psig. or lower. The lowest pressure of the available vent system may be used. The catalyst bed is then immersed in a hot hydrocarbon mixture, preferably one containing at least 5 wt.% aromatic hydrocarbons. This mixture is to have a temperature above about 280° F., and in the preferred embodiment above 325° F. to maintain the high temperature of the catalyst bed. This step is performed by passing the liquid hydrocarbon mixture upwardly into the catalyst bed. This is because when the liquid has been passed into the catalyst bed from the top, the results of the regeneration method have been inferior to those obtained with upward liquid flow into the reactor. The amount of liquid used must be enough to completely cover the catalyst bed, but the hydrocarbon mixture is not pumped through the catalyst bed and the catalyst bed is not agitated as in the prior art references. A pure hydrocarbon stream such as benzene, toluene or xylene may be used for this purpose, but it is preferred to use a less expensive hydrocarbon mixture. As it has been found to be effective and is often available in refineries, a stabilized reformate is the preferred liquid. This liquid is normally at the required temperature when it is withdrawn from the stabilizer column normally associated with the reforming operation.

The reactor and the catalyst bed are then pressurized to a pressure above 100 psig. The pressure imposed at this point is preferably above 150 psig. and more preferably 200 psig. or higher. The catalyst bed is then allowed to soak in the liquid hydrocarbon mixture at the previously described elevated temperatures. It is preferred that the initial soaking period be about 60 minutes, but soaking periods of about 10 to 120 minutes or longer may also be used. The pressure in the catalyst bed must be sufficient to maintain liquid phase conditions.

The reactor and catalyst bed are then once again depressurized to a pressure below about 10 psig. The quantity of hydrocarbon liquid which has been retained in the reactor is then drained from the catalyst, and a new quantity of the same fresh hot hydrocarbon liquid is passed into the reactor to once again immerse the catalyst bed. The temperature of the catalyst bed is to remain above about 280° F. during this draining and refilling of the reactor, and preferably above 325° F. To clarify this point, the temperature of the catalyst bed should be maintained above 280° F., and preferably above 325° F., at all times during the entire regeneration procedure. The reactor and the catalyst bed are then represented to the pressures previously specified, and the catalyst is once again soaked in the hot hydrocarbon liquid. The second soaking period is preferably shorter than the first soaking period. It may vary from about 10 to about 120 minutes or longer, but the preferred second soaking period is approximately 30 minutes. The reactor and catalyst bed is then once again depressurized to below about 10 psig. and drained of liquid.

A third soaking cycle is then performed by repeating the steps of the second soaking cycle. That is, the catalyst bed is once again immersed in fresh hot hydrocarbon liquid, pressurized and soaked for the shorter soaking period but at the same high temperatures, and then depressurized and drained. This final draining may be assisted by the use of an inert gas, such as nitrogen, to pressure any liquid from the reactor. At this point the still hot reactor can be pressurized and prepared for start-up. It has been found that the preferred regeneration method may be performed on commercial SPA catalyst units in a total time of about 6 to 8 hours. The method therefore allows the regeneration of the catalyst with only a minimal interruption of the operation of the unit.

The inventive concept is subject to the normal modifications which are required to adopt it for use on differing reactor and catalyst systems. Besides the previously described variation in hydrocarbon liquid composition, temperature, pressure and soaking period, the regeneration may be varied in such ways as repeating the soaking cycle for a fourth or fifth time. The regeneration method can be applied to a fixed bed of catalyst having essentially any configuration including those contained in tubular and chamber reactor systems and in reactors having more than one distinct catalyst bed. Unless otherwise specified, all catalyst bed temperatures are intended to indicate an average bed temperature obtained from a vertical catalyst bed temperature profile taken at an internal point within the catalyst bed.

We claim as our invention:

1. An in-situ method of regenerating a used fixed-solid phosphoric acid catalyst bed which has been deactivated by agglomerization of polymers formed during polymerization of an olefinic feed stream which comprises the steps of:
   a. terminating the flow of said olefinic stream through said catalyst bed, and then draining any liquid from said catalyst bed while maintaining said catalyst bed at a temperature above 280° F.;
   b. depressurizing said catalyst bed from a pressure above about 300 psig.; to a pressure below about 10 psig.;
   c. immersing said catalyst bed drained of said olefinic feed stream in a liquid hydrocarbon mixture containing at least 5 wt. % aromatic hydrocarbon and which has a temperature above 280° F., without a throughput of said hydrocarbon mixture through said catalyst bed and wherein said hydrocarbon mixture is ingressed to said catalyst bed from the bottom of said bed in an upwardly direction;
   d. pressurizing said catalyst bed to a pressure above 100 psig. and soaking said catalyst bed at a temperature over 280° F. for at least 10 minutes while said liquid hydrocarbon mixture is retained within said catalyst bed;
   e. depressurizing said catalyst bed to a pressure below about 10 psig. and draining said liquid hydrocarbon from said catalyst bed;
   f. repeating said steps (c), (d) and (e) twice; and,
   g. pressurizing said catalyst bed to the pressure at which said catalyst bed is placed in use.

2. The method of claim 1 wherein the catalyst bed is soaked for a period in excess of 30 minutes during the initial performance of step (d).

3. An in-situ method of regenerating a bed of used fixed-solid phosphoric acid catalyst which has been deactivated by agglomerization of polymers formed during polymerization of an olefinic feed stream which comprises the steps of:
   a. terminating the flow of said olefinic stream through said catalyst bed, and then draining any liquid from said catalyst bed while maintaining the catalyst bed at a temperature above about 325° F.;
   b. depressurizing the catalyst bed from a pressure above 400 psig. to a pressure below about 10 psig;
   c. immersing said catalyst bed drained of said olefinic feed stream in a substantially sulfur-free liquid hydrocarbon mixture containing at least 25 wt. % aromatic hydrocarbons and which has a temperature above about 325° F., without a throughput of said hydrocarbon mixture through said catalyst bed and wherein said hydrocarbon mixture is ingressed to said catalyst bed from the bottom of said bed in an upwardly direction;
   d. pressurizing said catalyst bed to a pressure above about 150 psig. and soaking said catalyst bed in said liquid hydrocarbon mixture at a temperature over about 325° F. for about 60 minutes;

e. depressurizing said catalyst bed to a pressure below about 10 psig. and draining said liquid hydrocarbon mixture from the catalyst bed;

f. repeating said steps (c), (d) and (e) twice with a reduced soaking period of about 30 minutes; and g. pressurizing said catalyst bed to the pressure at which the catalyst bed is placed in operation.

4. The method of claim 3 wherein the liquid hydrocarbon mixture is a stabilized reformate.

* * * * *

UNITED STATES PATENT AND TRADEMARK OFFICE
CERTIFICATE OF CORRECTION

PATENT NO. : 4,062,801
DATED : December 13, 1977
INVENTOR(S) : Vance P. Burton, Michael Z. Mikulicz It is certified that error appears in the above-identified patent and that said Letters Patent are hereby corrected as shown below:

The assignee is UOP Inc., Des Plaines, Illinois

Signed and Sealed this

Fifteenth Day of January 1980

[SEAL]

Attest:

SIDNEY A. DIAMOND

Attesting Officer     Commissioner of Patents and Trademarks